_United States Patent_ [19]

Vary et al.

[11] Patent Number: 5,030,574

[45] Date of Patent: Jul. 9, 1991

[54] PLASMIDLESS LAC STRAIN OF *BACILUS MEGATERIUM* QM B1551

[76] Inventors: Patricia S. Vary, 315 W. Prairie, Wheaton, Ill. 60187; Yi-Ping Tao, Apartment D-20, 510 Annie Glidden Rd., De Kalb, Ill. 60115

[21] Appl. No.: 64,842

[22] Filed: Jun. 19, 1987

[51] Int. Cl.$^5$ .................. C12N 1/20; C12N 15/00
[52] U.S. Cl. ..................... 435/252.31; 435/172.3; 435/252.5
[58] Field of Search ............ 435/68, 91, 172.1, 172.3, 435/252.3, 252.5, 252.31–252.35, 320, 837, 69.1, 71.2; 935/72–75

[56] References Cited

U.S. PATENT DOCUMENTS 4,190,495  2/1980  Curtiss, III ..................... 935/73

OTHER PUBLICATIONS

Stahl et al.; Chem. Abstr. 99: 100158v (1983).

Vary, P. S., Garbe, J. C., Franzen, M. A. and Frampton, E. W., 1982, MP13, A Generalized Transducing Bacteriophage for *Bacillus megaterium*, J. Bacteriol. 149:1112–1119.

Garbe, J. C. and Vary, P. S., 1981, Bacteriophage MP13 Transduction of *Bacillus megaterium* OM B1551, pp. 83–87, In: *Sporulation and Germination*, H. S. Levinson, A. L. Sonenshein and D. J. Tripper (eds.), American Society for Microbiology, Washington, D.C.

Callahan, J. P., Crawford, I. P., Hess, G. F. and Vary, P. S., 1983, Cotransductional Mapping of the trp–his region of *Bacillus megaterium*, J. Bacteriol. 154:1455–1458.

Garbe, J. C., Hess, G. F., Franzen, M. A. and Vary, P. S., 1984, Genetics of Leucine Biosynthesis in *Bacillus megaterium*, J. Bacteriol. 157:454–459).

Brown, B. J. and Carlton, B. D., 1980, Plasmid Mediated Transformation in *Bacillus megaterium*, J. Bacteriol. 142:508–512.

Vorobjeva, I. P., Khmel, I. A. and Alfoldi, L., 1980, Transformation of *Bacillus megaterium* Protoplasts by plasmid DNA, FEMS Microbiology Letters, 7:261–263.

Kieselburg, M. K., Weikert, M. and Vary, P. S., Analysis of Resident and Transformant Plasmids in *Bacillus megaterium*, Bio/technology, 2:254–259.

Bohall, N. A., and Vary, P. S., Transposition of Tn917 in *Bacillus megaterium*, J. Bacteriol. 167:716–718.

Von Tersch, M. A. and Carlton, B. C., 1984, Molecular Cloning of Structural and Immunity Genes for Megacins A-216 and A-19213 in *B. megaterium*, J. Bacteriol. 160:854–859.

Weiland, Katherine Lee, M. S. Thesis, Department of Biological Sciences, Northern Illinois University, Plasmid Analysis of Megacin Negative Strains of *Bacillus megaterium* QM B1551.

*Primary Examiner*—James Martinell
*Attorney, Agent, or Firm*—Grace J. Fishel

[57] ABSTRACT

A plasmidless Lac mutant strain of *Bacillus megaterium* QM B1551 designated PV447 is provided which otherwise has substantially all of the characteristics of the parent stock.

*B. megaterium* PV447 has been deposited at the NRRL on June 19, 1987 and been given NRRL accession No. B-18233.

2 Claims, 1 Drawing Sheet

PLASMIDLESS LAC STRAIN OF *BACILUS MEGATERIUM* QM B1551

The invention described herein was made partly in the course of work under a grant(s) or award(s) from the National Science Foundation.

BACKGROUND OF THE INVENTION

1. Field of the Invention

The present invention relates to a plasmidless Lac⁻ strain of *Bacillus megaterium* QM B1551 for use as a bacterial cloning host for recombinant plasmids.

*B. megaterium* has been the object of study in many laboratories both for its interesting biochemical reactions, and because it germinates synchronously and sporulates more efficiently than most other *Bacillus* species. Industrially, *B. megaterium* has been used to produce L-glutamate, pyruvate, cobalamin, single cell protein, and to modify steroids and antibiotics. Up until the present time, however, *B. megaterium* has not been used as a cloning host to any great extent, a function for which another member of the *Bacillus* species, *Bacillus subtilis*, and *Escherichia coli* have been widely used.

As a cloning host, *E. coli* has a number of shortcomings which are not common to *B. megaterium*. For example, *E. coli* do not secrete proteins in any great quantity and the outer membrane includes an endotoxin. A genetically engineered clone of *E. coli* must therefore be lysed to recover a protein of interest which is often then contaminated with endotoxins. *B. megaterium*, on the other hand, is an efficient secretor of protein and has no endotoxins in the cell wall, making it more suitable for mass production of pharmaceuticals. While "safe" strains of *E. coli* have been developed, "wild" *E. coli* is a human pathogen whereas *B. megaterium* like *B. subtilis* is not.

*B. subtilis* secretes proteins readily but has two different types of extracellular proteases which digest most protein expressed by the cell, greatly decreasing the yield of the protein of interest. Insofar as known, all protease negative mutants of *B. subtilis* are leaky while *B. megaterium* has only one extracellular protease and some strains are protease negative.

Even though *B. megaterium* has a number of advantages over *E. coli* and *B. subtilis*, it has a number of disadvantages which have stood in the way to its use as cloning host. Firstly, it is not as well characterized genetically and, secondly, it contains a large number of naturally-occurring plasmids which potentially might interfere with the expression or further genetic manipulation of any foreign plasmid DNA.

2. Brief Description of the Prior Art

In the past few years, our laboratory has made considerable progress in understanding *B. megaterium* QM B1551 genetically. We have isolated and characterized a generalized transducing phage for this species, which has been used almost exclusively for mapping in QM B1551, and have mapped in detail several loci. (Vary, P. S., Garbe, J. C., Franzen, M. A. and Frampton, E. W. 1982. MP13, A generalized transducing bacteriophage for *Bacillus megaterium*. J. Bacteriol. 149:1112-1119; Garbe, J. C. and Vary, P. S. 1981. Bacteriophage MP13 transduction of *Bacillus megaterium* QM B1551, p. 83-87. In: *Sporulation and Germination*. H. S. Levinson, A. L. Sonenshein and D. J. Tripper (eds.), American Society for Microbiology, Washington, D. C.; Callahan, J. P., Crawford, I. P., Hess, G. F. and Vary, P. S. 1983. Cotransductional mapping of the *trp-his* region of *Bacillus megaterium*. J. Bacteriol. 154:1112-1116 and Garbe, J. C., Hess, G. F., Franzen, M. A. and Vary, P. S. 1984. Genetics of leucine biosynthesis in *Bacillus megaterium*. J. Bacteriol. 157:454-459.

In 1980 other laboratories reported protoplast transformation in *B. megaterium* 216 with a few naturally-occurring plasmids from Bacillus and Staphylococcus. (Brown, B. J. and Carlton, B. C. 1980. Plasmid mediated transformation in *Bacillus megaterium*. J. Bacteriol. 142:508-512 and Vorobjeva, I. P., Khmel, I. A. and Alfoldi, L. 1980. Transformation of *Bacillus megaterium* protoplasts by plasmid DNA. FEMS Microbiology Letters. 7:261-263). Thereafter, we began to analyze the resident plasmids in *B. megaterium* QM B1551, in which all of the genetic mapping had been done with MP13, and to extend the transformation studies to test the stability of foreign plasmids in QM B1551.

In 1984, we published an article (Kieselburg, M. K., Weickert, M. and Vary, P. S. Analysis of resident and transformant plasmids in *Bacillus megaterium*. Bio/Technology 2:254-259) reporting that the resident plasmids of QM B1551 had been analyzed and that several Bacillus cloning plasmids had been successfully transformed into QM B1551 by protoplast fusion. More particularly, we analyzed the plasmid array of *B. megaterium* QM B1551 by sucrose gradient centrifugation, agarose gel electrophoresis and electron microscopy measurements and found seven plasmid sizes ranging in molecular weight from $3.5$ to $109 \times 10^6$. The plasmids transformed by protoplast fusion were found to be stable and present in high copy number suggesting that *B. megaterium* QM B1551 might be a desirable cloning host.

Since the use of transposons greatly increases the genetic versatility of an organism, we continued our work with *B. megaterium* QM B1551 by testing whether a transposon could be introduced into QM B1551. In 1986, we reported that transposon Tn917, carried on plasmid pTV1, had been successfully introduced into QM B1551 and transposed efficiently and apparently without hot spots. (Bohall, N. A. and Vary, P. S. Transposition of Tn917 in *Bacillus megaterium*. J. Bacteriol. 167:716-718)

Because at least 11% of the cellular DNA of *B. megaterium* QM B1551 is present as plasmid DNA, for QM B1551 to have prospects for use industrially as a cloning host, it was necessary to cure QM B1551 of its plasmids as they are sufficiently numerous as to be likely to interfere with any foreign plasmids introduced into the cell. Having proved the stability, of foreign plasmids in *B. megaterium* QM B1551 and the use of transposon, our attention was now directed to the development of a plasmidless strain.

In earlier work, another laboratory isolated a plasmidless strain of *B. megaterium* 19213, designated VT1600 (ATCC 35985) (Von Tersch, M. A. and Carlton, B. C. 1984. Molecular cloning of structural and immunity genes for megacins A-216 and A-19213 in *B. megaterium*. J. Bacteriol. 160:854-859) but they did not test for expression of recombinant proteins, nor did they develop a Lac⁻ strain. Almost all of the genetic techniques and methods in *B. megaterium* have been developed in QM B1551 and the use of Lac fusions greatly increases the genetic versatility of an organism. To use this technique with *B. megaterium*, it was essential that a Lac⁻ strain be developed of a *B. megaterium* strain which is well mapped and which is otherwise suitable as a cloning host.

It view of the above, it is an object of the present invention to provide a plasmidless Lac⁻ strain of *B. megaterium* QM B1551 in which Lac fusions can be done and in which, like the parent stock, foreign plasmids are stable and transposons can be introduced efficiently and randomly. It is another object to provide a plasmidless Lac⁻ strain which retains the parent stock's neutral protease. Other objects and features of the invention will be in part apparent and in part pointed out hereinafter, the scope of the invention being indicated by the subjoined claims.

SUMMARY OF THE INVENTION

A novel plasmidless Lac mutant strain of *B. megaterium* QM B1551 is provided which can be used as a bacterial cloning host for recombinant plasmids. A method for producing the mutant strain and a utility are described.

DETAILED DESCRIPTION OF THE INVENTION

Figure 1:
FIG. 1 shows *B. megaterium* mutant PV447, its parent and lacZ containing plasmid transformants clockwise from white colony: PV477 (lac-3 lac-6) white on LB-Xgal medium. PV415(lac-3) the blue parent of PV447;PV361: plasmidless parent of PV415; QM B1551: wild type parent of PV361; RV/pCED6-81, a lacZ *E. coli* mutant containing a plasmid with an active lacZ fusion; PV471 and PV472: two transformants of PV447 containing plasmid pTV32, which has a promoterless lacZ gene, but shows slight read-through (light blue) from an exogenous promoter PV470 and PV469: PV447 carrying plasmid pTV53, similar to pTV32.
Figure 1:
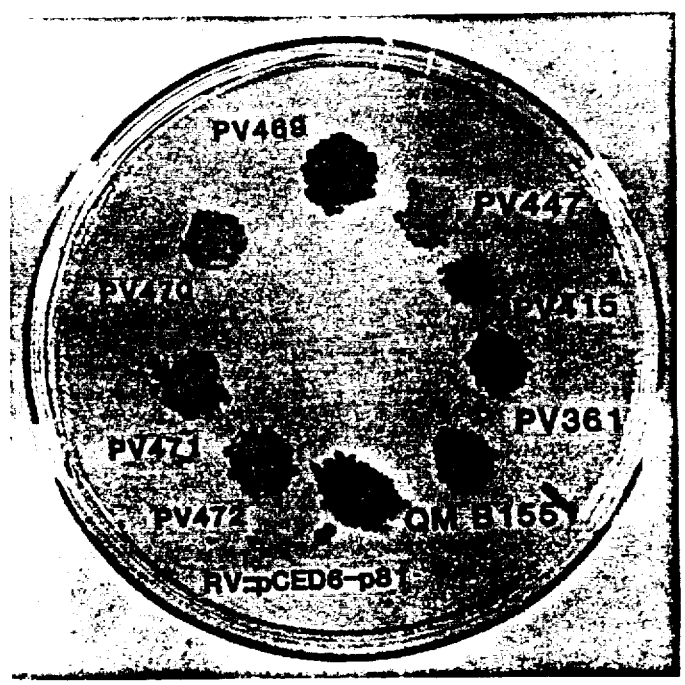

As those skilled in the art know, producing a plasmid-negative variant of a known organism is an empirical process making use of natural variants as may result by point mutations, phase variations and deletions, in addition to selective or mutagenic effects (or both) which are the result of various physical and/or chemical agents. In advance, it is difficult to predict which condition or combination of conditions will result in a plasmidless strain or, for that matter, that any condition will produce such a strain and the curing of a strain having seven different sizes of plasmids is particularly speculative. It is also difficult to predict what other genetic changes may occur and to what extent the mutant strain will resemble the parent stock. Typical physical and chemical agents include elevated temperature, thymine starvation, chemical mutagens, ultraviolet light, nickel and cobalt, acridines and other intercalating dyes and so forth. Such a process is called "curing" and may be taken to mean that the plasmid is selectively inactivated or that it is inhibited in replication. For our purpose, we use the term in the more restrictive sense that the plasmid has been inhibited in replication and therefore absent from the daughter cell.

As applied to QM B1551, we discovered that exposure of the parent strain to a sublethal concentration of a chemical mutagen at elevated temperatures produced a number of strains, some of which were cured of all but a few plasmids. More particularly, strain PV361 was produced from a culture of *B. megaterium* QM B1551 grown in supplemented nutrient broth containing per liter 8 g of nutrient broth (Difco Laboratories), 1 g of glucose, 13.4 mM KCl, 0.02 mM $MnCl_2$, 1 $\mu$M $FeSO_4$, 1 mM $MgSO_4$ and 1 mM $CaCl_2$. Growth was continued to an absorbance at 660 nm in a 1 cm light path of 6.8-8.0. The culture was diluted to $10^{-3}$ cells/ml in MC broth and 0.1 ml was then added to 0.9 ml of SNB broth containing a concentration of ethidium bromide in an amount from about 5 to about 200 ng/ml as a curing agent. More particularly, the concentrations of ethidium bromide used were 0.5, 1.0, 2.0, 10.0, 20.0, 100 and 200 ng/ml. The tubes were then incubated with shaking at an elevated temperature between about 30° and about 50° C.—namely, at 37° and 44° C. for 24 hours. The tubes having the highest concentrations of curing agent that allowed growth were diluted and streaked on SNB plates. Single colonies were then picked to master plates, allowed to sporulate and the spores stored on disks and frozen.

Portions from each stored strain were streaked on SNB plates, incubated at 30° C. overnight and subjected to agarose gel electrophoresis under the same conditions as described for QM B1551 in our above-mentioned article in Bio/Technology to determine the presence and estimated size of any remaining plasmids. Various strains were found to have been cured of various of the plasmids.

One strain in particular designated PV200 derived from QM B1551 treated with ethidium bromide at a concentration of 1.0 ng and at a temperature of 44° C., was found to have been cured of all but three plasmids—namely, pVY105, pVY113 and pVY132. With the passage of time and/or with subsequent platings on SNB, PV200 spontaneously lost its remaining plasmids and became a plasmidless strain which was designated PV361.

Strain PV361 was Lac+ and was further mutagenized once with nitrosoguanidine at a concentration of 100 ag for 30 minutes to select a mutant unable to grow on a minimal medium containing per liter 5 g of lactose, 2 g of $(NH_4)_2SO_4$, 6 g of $KH_2PO_4$, 14 g of $K_2HPO_4$, 1 g of trisodium citrate$\cdot 2H_2O$, 0.2 g of $MgSO_4 \cdot 7H_2O$, 3.6 $\mu$M $FeCl_2$, 0.1 mM $MnCl_2$ and 0.1 mM $CaCl_2$. However, this mutant, which was designated PV415(lac-3) was still blue on LB-Xgal indicator plates fluoresced in UV light in the presence of methyl umberliferol galactoside (MUG). Another mutagenesis with UV at a wavelength of about 280 nm for 20 seconds at 4.8J/m²/sec and screening on LB-Xgal produced a plasmidless Lac⁻ Mutant, designated PV447(lac-3 lac-6). A biologically pure strain of PV447 is available in the Agricultural Research Service Culture Collection at the Agricultural Research Culture Collection (NRRL) International Depositary Authority, 1815 N. University Street, Peoria, Ill. 61604, U.S.A. under NRRL accession No. B-18233.

PV447 grows like and its protoplasts can be transformed as well as *B. megaterium* QM B1551. Examples of PV447 carrying various plasmids are shown in FIG. 1. Transposition experiments were performed on PV447 using plasmid pTV53(tet Tn917 LacZ-cat-MLS') and pTV32 (cat Tn917(lacZ MLS'). By screening pTV53 transpositions on LB-Xgal and chloramphenicol for blue on LB-Xgal and chloramphenicol sensitivity (i.e. a late expressing gene) and by MUG, a spo $\Omega$Tn917 lacZ cat fusion mutant was isolated that expressed $\beta$-galactosidase late in the stationary phase, thus confirming that PV447 is useful as a bacterial cloning host for recombinant plasmids. PV447 has lost its ability to produce extracellular megacin, which is one less protein that needs to be eliminated during purification of recombinant proteins, but it produces a neutral protease like QM B1551 and otherwise has the same characteristics of the wild strain from which it was derived.

In view of the above, it will be seen that the several objects of the invention are achieved and other advantageous results attained.

What is claimed is:

1. A plasmidless Lac⁻ culture of *Bacillus megaterium* derived from *Bacillus megaterium* QM B1551 which is deposited under NRRL accession No. B-18233 in the Agricultural Research Service Culture Collection.

2. A transformed host cell comprising *Bacillus megaterium* QM B1551 (NRRL B-18233) and further comprising a foreign plasmid.

* * * * *

UNITED STATES PATENT AND TRADEMARK OFFICE
CERTIFICATE OF CORRECTION

PATENT NO. : 5,030,574

DATED : July 9, 1991

INVENTOR(S) : Patricia S. Vary and Yi-Ping Tao

It is certified that error appears in the above-identified patent and that said Letters Patent is hereby corrected as shown below:

The Sheet of Drawing consisting of Fig. 1 should be deleted to appear appear as per attached sheet.

Signed and Sealed this

Twenty-fourth Day of November, 1992

Attest:

DOUGLAS B. COMER

Attesting Officer    Acting Commissioner of Patents and Trademarks